United States Patent [19]

Friedman

[11] Patent Number: 5,693,077
[45] Date of Patent: Dec. 2, 1997

[54] TREATMENT OF VASCULAR AND TENSION HEADACHE ATYPICAL FACIAL PAIN ALLERGIC RHINITIS AND CERVICAL MUSCLE HYPERACTIVITY

[76] Inventor: Mark H. Friedman, 660 Gramatan Ave., Mt. Vernon, N.Y. 10552

[21] Appl. No.: 593,137

[22] Filed: Feb. 1, 1996

Related U.S. Application Data

[62] Division of Ser. No. 311,009, Sep. 21, 1994, Pat. No. 5,527,351.
[51] Int. Cl.$^6$ ...................................................... A61F 7/00
[52] U.S. Cl. ........................... 607/96; 607/104; 606/20
[58] Field of Search ...................... 606/20–26; 607/96, 607/104, 105, 113, 108–112, 114

[56] References Cited

U.S. PATENT DOCUMENTS

| 697,181 | 4/1902 | Smith | 607/105 |
|---|---|---|---|
| 3,924,628 | 12/1975 | Droegemuller et al. | 607/105 |
| 4,638,806 | 1/1987 | Bartlett | 607/105 |
| 4,946,460 | 8/1990 | Merry et al. | 606/24 |
| 5,005,587 | 4/1991 | Scott | 607/125 |
| 5,423,807 | 6/1995 | Milder | 607/105 |
| 5,423,811 | 6/1995 | Imran et al. | 607/105 |

Primary Examiner—Robert Nasser
Attorney, Agent, or Firm—Evelyn M. Sommer

[57] ABSTRACT

A new non-invasive, non-toxic, non-sedating method for treatment of vascular headaches (migraine and cluster), tension headache, atypical (chronic) facial pain, allergic rhinitis and cervical muscle spasm is presented. This method comprises the application of cold or frozen water or saline (0°–4° C.), cold metal, or ice to the area of tenderness associated with the plexus formed by the posterior and middle superior alveolar branches of the ipsilateral maxillary nerve, as well as to other branches of the trigeminal nerve. The cold or frozen water or saline can be applied indirectly when contained in small bags, tubes or packs made of plastic film, latex, silicone, or the like. Metal tubes can also be used which have been chilled by either running cold water or ice through their hollow interiors. Preferably plastic tubes encasing a column of ice, which ice can be extruded gradually by the patient or clinician by means of a plunger inserted into the tubes are used. Alleviation of pain is noted within a short period of the onset of the treatment. Repeated treatment even during pain-free periods offers protracted benefits, i.e., prevention or amelioration of the headaches or other conditions.

1 Claim, 6 Drawing Sheets

TREATMENT OF VASCULAR AND TENSION HEADACHE ATYPICAL FACIAL PAIN ALLERGIC RHINITIS AND CERVICAL MUSCLE HYPERACTIVITY

This is a division of application Ser. No. 08/311,009 filed Sep. 21, 1994, now U.S. Pat. No. 5,527,351.

The present invention relates to a new method for treatment of vascular (migraine, cluster) and tension headache, chronic facial pain, cervical muscle hyperactivity (spasm) and allergic rhinitis.

The method is non-invasive, non-toxic, and non-sedating.

The method of the invention comprises the application of cold water, ice, or frozen saline (0°–4° C.) to an area of intra-oral tenderness which has been found to be associated with the above conditions. This zone of tenderness was observed by the inventor to be in the area of the plexus formed by the posterior and middle superior alveolar branches of the ipsilateral maxillary nerve and is bilateral when the symptoms are bilateral.

The cold water, frozen saline, or ice is applied indirectly to the maxillary nerve (V2), a division of the trigeminal nerve, by application of the cold water or chilled or frozen saline contained in small bags, tubes or packs, by perfusing cold water through hollow metal tubes, or by direct application of ice contained in hollow plastic or metal tubes and extruded onto the area. In the latter instance a device is preferably provided wherein the ice can be extruded gradually by the patient or physician in contact with the area overlying the nerve. This treatment produces a marked decrease or elimination of the intra-oral maxillary tenderness and, with repeated applications, a decrease in frequency and severity of headaches. When the patient is symptomatic, headache, facial pain, and cervical spasm relief occurs often in a matter of seconds. If the pain returns, or to provide more long lasting relief, the procedure is repeated.

Headaches can be classified into three main groups: muscle contraction (tension-type), vascular (migraine, cluster), and traction and inflammatory headaches. The latter group may be caused by stroke, hypertension, hemorrhage from an aneurysm, brain tumor, infections, or inflammation.

Tension-type headache (new International Headache Society classification), formerly referred to as muscle contraction headache, is by far the most common headache. This condition is divided into two major categories, episodic tension-type headache and chronic tension type headache. The former is the familiar ailment that virtually everybody experiences occasionally. The latter condition may be related to migraine. It is characterized by daily or almost daily discomfort with superimposed migrainous events at varying frequencies, and may be the most common problem seen at headache centers. Patients complain of daily headache, which comprises dull to moderate discomfort most of the time, except for several days during the month when the patients are partially or completely incapacitated. At such time, the pain is associated with typical migrainous symptoms such as nausea, and vomiting, photophobia, and other descriptors of migraine. Patients usually complain of pain and tightness in the frontal, temporal and/or occipital areas. Pain in the latter area may indicate cervical involvement. The definition of "tension-type" headache is confusing, because it does not distinguish between psychological tension and muscle tension induced headache. Most authorities believe that psychological factors, including stress, cause muscle tension which produces the headache. Additionally, many of these patients exhibit significant cervical muscle spasm and/or inflamed cervical joints often associated with arthritis, which can refer directly as tension-type headache. Other factors such as postural deformities or poor work habits can also contribute to the headache directly or by causing adjacent craniofacial muscle spasm or temporal muscle joint inflammation, thereby contributing indirectly to the tension-type headache.

Treatment for headache includes physical therapy, biofeedback, chiropractic, counseling, and medication. The latter includes analgesics, muscle relaxants, tranquilizers, and antidepressants. Combination drugs are widely used. Many of these patients tend to abuse a wide variety of medications, including both prescription and non-prescription drugs. Overuse often leads to an analgesic rebound headache or the worsening of the head pain caused by the frequent and excessive use of analgesics.

Migraine is the most common headache which causes patients to consult a physician. Based largely on data drawn from the American Migraine Study, in which over 20,000 respondents returned questionnaires mailed to their households, the results indicate migraine occurs in 17.6% of females and 6% of males in the United States. Considering this incidence, the economics of migraine in time lost from work, inefficiency, etc. is substantial. Effective treatment increases the patient's ability to live a normal and productive life. In addition to pain, the symptoms most commonly associated with migraine include nausea and vomiting, photophobia, phonophobia, anorexia, pallor, and a desire to lie down. If symptoms are preceded by or associated with visual symptoms such as flashing lights, black spots or partial visual field loss, the migraine is classified as classic, as opposed to the previously described common migraine.

Multiple humoral agents have been postulated as being the major factor in migraine. These include serotonin, histamine, prostaglandins, platelet factors, endorphins, and vasoactive neuropeptides. The etiology of migraine has been studied by many investigators. Present research no longer supports the vasodilator/vasoconstrictor mechanism of vascular headache, i.e., arterial dilation causes pain and constriction equals relief. Research has now implicated a sterile inflammation, possibly occurring in the meninges (pia mater, dura mater, arachnoid), as the causative factor for vascular head pain. An unknown trigger activates perivascular trigeminal axons, which release vasoactive neuropeptides (substance P, calcitonin gene-related peptide, etc.). These agents produce the local inflammation i.e., vasodilation, plasma extravasation, mast cell degranulation which cause transmission of impulses to the brain stem and higher centers which in turn register as head pain (Moskowitz MA, Trends in Pharmacological Sciences, August 1992).

Migraine therapy is either prophylactic or symptomatic. Prophylactic medication may be selected for a patient having two to four or more headaches per month, if they are severe enough to interfere with daily activities. Beta blockers such as propranolol (Inderal) are the most commonly used. Other medications frequently used include serotonin antagonists such as methysergide maleate (Sansert), calcium channel blockers (Verapamil), amytryptyline (Elavil), and ergotamine preparations with belladoric alkaloids and phenobarbital. All of these medications have significant side effects including sedation, loss of energy and drive, dry mouth, constipation, weight gain, and gastrointestinal cramping and distress. For symptomatic treatment, ergotamine with caffeine (cafergot) is commonly used. Other medications employed for treating migraine include isometheptene mucate (Midrin), NSAID's (Motrin, Naprosyn, etc.), dihydroergotamine and the newer medication sumatriptan (Imitrex) some of which must be injected intramuscularly. When narcotics, such as Fiorinal with codeine are used frequently, additional hazards, including the considerable potential for rebound headaches and habituation are encountered.

Cluster headaches occur much less frequently than migraine, and mostly (90%) in men, who usually complain of severe unilateral eye pain, ptosis (drooping eyelid), eye tearing, and nasal congestion and/or discharge. Unlike migraine patients who feel more comfortable when lying down, these patient's symptoms usually increase in a supine position. These relatively brief but severe headaches occur daily (or even more frequently) during the cluster period, which may last for several months.

The mechanism for cluster headache may be a pathophysiologic event occurring within the intracavernous carotid artery that activates nerve fibers within the pericarotid plexus. This plexus receives axonal projections from V1 and V2, superior cervical ganglia (sympathetic), and sphenopalatine (parasympathetic) ganglia. Trigeminal projections are activated to transmit impulses centrally and mediate periorbital; retro-orbital, and forehead pain.

Cluster headache therapy includes: steroids (Prednisone), Sansert, Verapamil, various ergot compounds, and lithium (for chronic cluster headaches). All of these medications can produce serious side-effects and complications. Inhalation of oxygen at the headache onset has been found, in some cases, to abort the headache.

Other modes for treating these various types of headaches include: (a) acupuncture, (b) biofeedback, and (c) chiropractic. However, studies have failed to show that any of these treatments is more effective than placebo. Acupuncture requires a highly-trained therapist. Biofeedback and particularly, training in muscular relaxation may be helpful for tension-type headache in selected individuals, but controlled studies have not demonstrated consistent success in the above conditions.

Atypical facial pain, which has recently been classified as facial pain by the International Headache Society, manifests itself as a relatively constant, mostly unilateral, at least initially, pain and appears unrelated to jaw function. This condition is not associated with sensory loss or other physical signs, and radiographic and laboratory studies are uniformly negative. This condition may occur as a residual from relatively uncomplicated dental work, but usually the cause is unknown. Many neurologists regard this condition as psychogenic. Amitriptyline at bedtime and/or various analgesics and narcotics are used, but atypical facial pain responds poorly to all forms of medication.

Cervical muscle hyperactivity (spasm), is an extremely common condition with many causes, including tension, response to an inflamed or subluxed joint, arthritic changes, poor posture or work habits, trauma, systemic disease and adjacent pathology. Common treatment modalities are physical therapy, chiropractic, and medications including muscle relaxants, NSAID's, analgesics, and antidepressants in small doses. Often despite all efforts made to alleviate this type of spasm, the condition becomes chronic. When a cervical joint becomes subluxed, it causes pain and restricted motion, local inflammation, and adjacent muscle spasm. Manipulation to unlock the joint is indicated but muscle spasm must be reduced first. Conventional methods of treatment include heat, ultrasound, electrogalvanic stimulation and massage. All of these methods are obviously time consuming. The relation between the condition of cervical muscle spasm and the previously described headaches and facial pain can be demonstrated by the fact that the headache and facial pain patients do not respond as well to treatment in the presence of significant cervical muscle spasm. One reason may be entrapment of the greater occipital nerve brought about by semispinalis muscle spasm. This greater occipital nerve supplies the cranial vertex. More importantly, present headache theory recognizes the sympathetic nervous system influence on headaches. In cases of significant cervical spasm, the superior cervical ganglion is likely to be mediating the neurogenic inflammation.

The need for a more appropriate method of treating vascular and tension headaches, atypical facial pain, and cervical muscle spasm is apparent as the current methods of treatment are often ineffective. Treatment with pharmacological agents is associated with toxicity and must be used systemically over prolonged periods of time and often for decades. These agents further do not meet with patient acceptance or compliance. The conditions herein described represent a tremendous economic loss, considering the number of individuals afflicted, the time lost from work, as well as the inability to enjoy a normal pain-free life.

Even though present research has strongly implicated a sterile perivascular inflammation as responsible for vascular headaches, the postulated site for this occurrence, the meninges, has not been confirmed.

The inventor's research strongly, suggests that this phenomenon occurs elsewhere and specifically in the previously described ipsilateral maxillary nerve plexus, and that it is also implicated in tension headaches and atypical facial pain, and somewhat related to cervical muscle spasm and allergic rhinitis (nasal congestion without radiographic or other causal evidence). It is likely that mild edema occurs in the maxillary nerve plexus microcirculation, caused by vasodilation and increased vascular permeability. This edema causes pressure on nerves which creates local tenderness. Because of this area's relative accessibility, the inventor has found it possible to consistently demonstrate several elements of local sterile inflammation: (1) normal appearing tissue, (2) consistent tenderness which is strongly related to symptoms, (3) increased temperature, and (4) positive response to cold.

No obvious tissue pathology or periodontal condition was noted in examination of over 800 patients with the above conditions. Even periodontal lesions of the maxillary molars, present in a few of these 800 patients (n=6) were located much closer to the gingival line, and appeared unrelated to the maxillary tender zone in the area of the root apices.

In one procedure carried out by blinded, inexperienced observers, they correctly identified the symptomatic side in 178/200 (89%) of symptom-free migraine and cluster headache patients by intra-oral palpation to determine the laterality of the maxillary tenderness. In studies conducted under the inventor's supervision, in over 90% of headache and facial pain patients observed by experienced investigators, ipsilateral tenderness, even in the symptom-free state, was found in patients presenting histories of such symptoms. It was found that bilateral symptoms produced bilateral tenderness, directly proportional to symptom severity. Tension headache usually occurs bilaterally, and these cases invariably demonstrated bilateral tenderness. The tender zone in patients with cervical muscle spasm was similarly symptom-related. In 36/38 tension headache patients experiencing unilateral symptoms a 94.7% correlation was found between laterality of symptoms and tenderness. The tender zone in patients with cervical muscle spasm was similarly symptom related.

Temperature increase was also associated with intra-oral maxillary tenderness. In fifty consecutive patients with complete or significant unilaterality of tenderness/symptoms, ipsilateral intra-oral maxillary zone temperature was demonstrably higher than on the contralateral side in 44/50 cases. A model YSI (Yellow Spring Instrument Co.) 43TA tele-thermometer with 406 probe was used. May of these headache and facial pain patients (n=31) were tender but Dot symptomatic at the time of the temperature determination. Significantly, the temperature differential between left and right sides appeared directly proportional to degree of tenderness and severity of symptoms. In extreme, cases, the temperature differential between left and right sides was as much as 1.5 degrees Fahrenheit. In 15 consecutive normal patients, no symptoms or tenderness, left and right temperatures were found to be nearly or completely identical.

In accordance with the invention, there is disclosed a method for treating vascular and tension headaches, atypical facial pain, cervical muscle hyperactivity and allergic rhinitis comprising the application of cold to the area of tenderness associated with the plexus formed by the posterior and middle superior alveolar branches of the ipsilateral nerve, as well as to other branches of the trigeminal nerve.

The application of cold, as hereinafter described, was utilized in over 500 in-office procedures to symptomatic patients. Significant or total relief was obtained in over 76% of the patients. Forty patients self treated at home, with ice filled plastic tubes, applied to the zone of tenderness obtained symptomatic relief. Daily applications, whether or not the patient was symptomatic, resulted in improvement, i.e., a decrease in the frequency, intensity or duration of headaches or facial pain in over 50% of patients.

It is theorized that the lowered tissue temperature reduces the plasma extravasation (edema) and thereby reduces pressure on the maxillary nerve. Because the sympathetic division of the autonomic (involuntary) nervous system is closely related to the trigeminal system, prolonged application of cold also appears to affect the sympathetic outflow via the cervical ganglion. In the majority of patients with cervical symptoms and tenderness, a significant relaxation of symptoms, decreased cervical tenderness, and increased cervical range of motion during cold application was noted.

This invention will be further explained in reference to the figures wherein.

Clinical evaluation of a non-invasive, non-toxic, non-sedating method for treatment of migraine and tension headache, atypical (chronic) facial pain, and cervical muscle spasm which comprises the application cold water or chilled saline (0°–4° C.), cold metal or ice to the area of tenderness associated with the plexus formed by the posterior and middle superior alveolar branches of the ipsilateral maxillary nerve, as well as to other branches of the trigeminal nerve was carried out.

In over 500 in-office applications to symptomatic patients with the above conditions, significant or total relief was obtained in over 76% of the patients. Each of the applications ranged from about 30 to about 50 seconds and was carried out with the small plastic packets, to about 2 to about 4 minutes when the plastic metal tubes were used, and up to about 14 minutes (usually bilaterally) with the flowing cold water. Daily applications, whether or not the patient was symptomatic, appeared to have protracted benefits. Frequency, intensity, or duration of headaches or facial pain improved in over 50% of patients. Most significant improvement occurred when the plastic ice-filled tubes were used, bilaterally by the patient at home for about four minutes.

Results of the clinical evaluations provided information in support of the proposed neurologic and physiologic mechanism of the pain associated with migraine and tension headaches, atypical facial pain and cervical muscle pain and spasm. Because of the relative accessibility of the maxillary nerve plexus, it was possible to consistently demonstrate several elements of local sterile inflammation, i.e., (1) normal appearing tissue, (2) consistent tenderness in that area that was strongly related to symptoms, (3) increased temperature associated with area of tenderness, and (4) positive response to treatment with cold.

Figure 1:
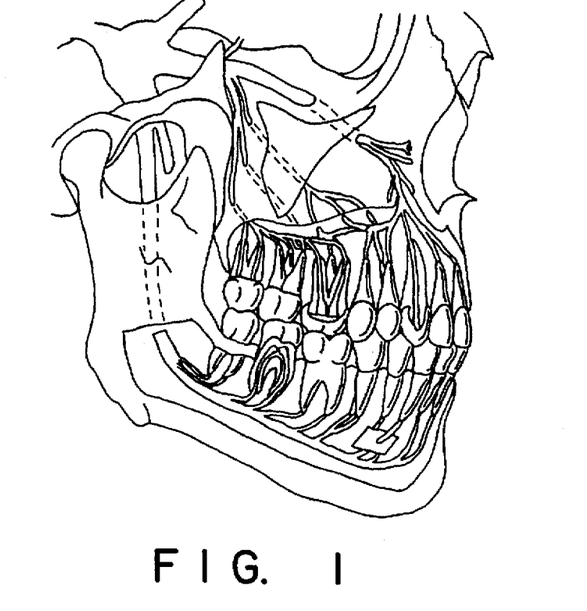
FIG. 1 illustrates the distribution of the trigeminal nerve.
Figure 2:
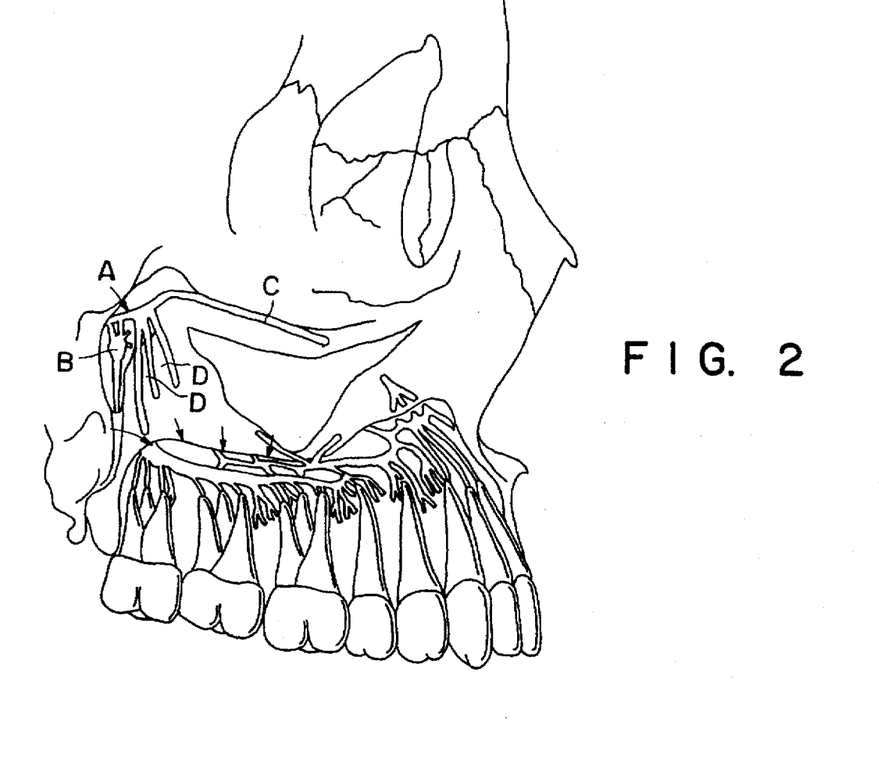
FIG. 2 illustrates the maxillary division (V2) of the trigeminal nerve.
Figure 3:
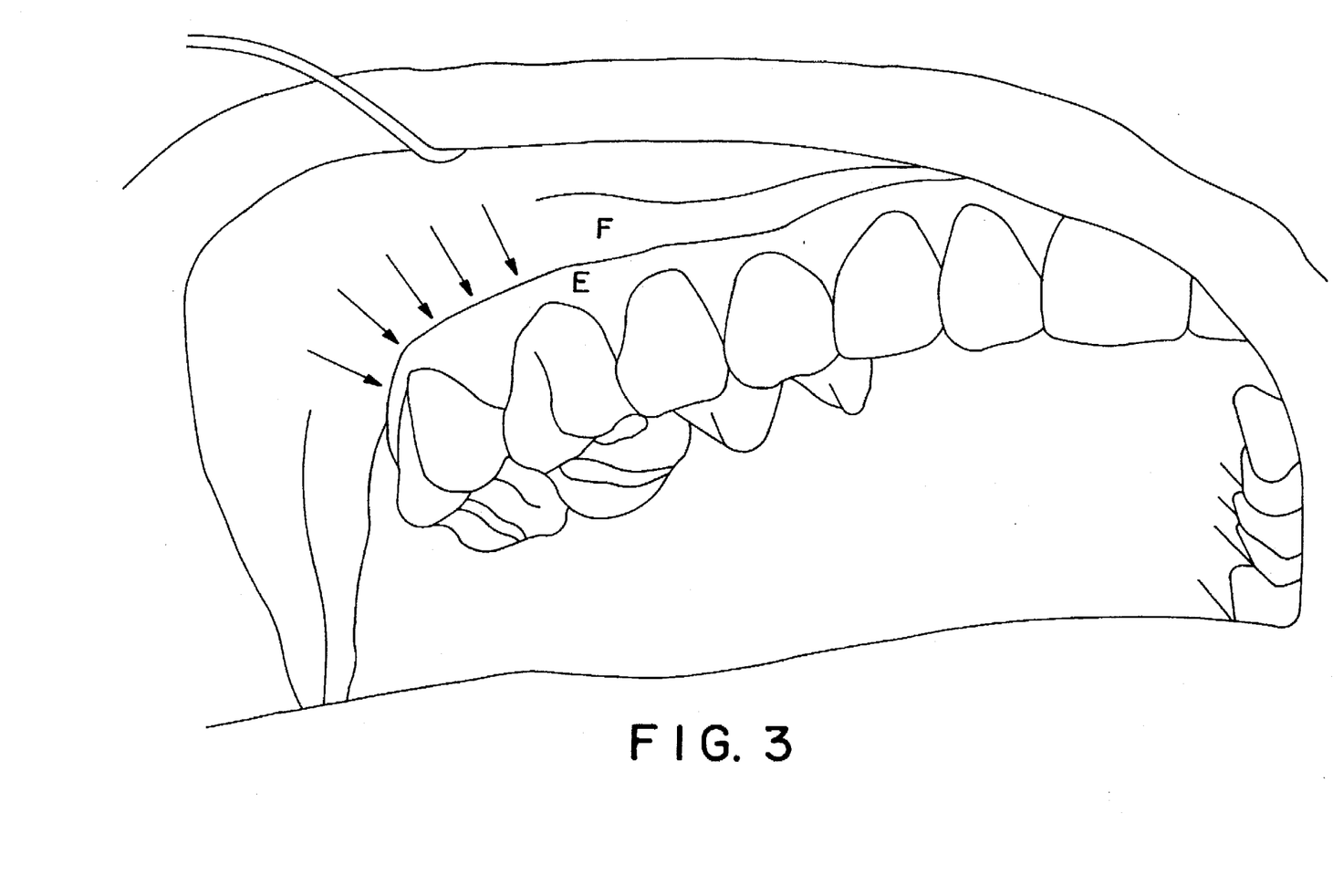
FIG. 3 illustrates the location of the intra-oral zone of maxillary tenderness.

FIGS. 1–3 are anatomical drawings. FIGS. 1–2 show the distribution of the trigeminal nerve and the maxillary division (V2) of the trigeminal nerve, respectively. FIG. 3 illustrates the location of the intra-oral zone of maxillary tenderness of one side of the face.

Figure 4:
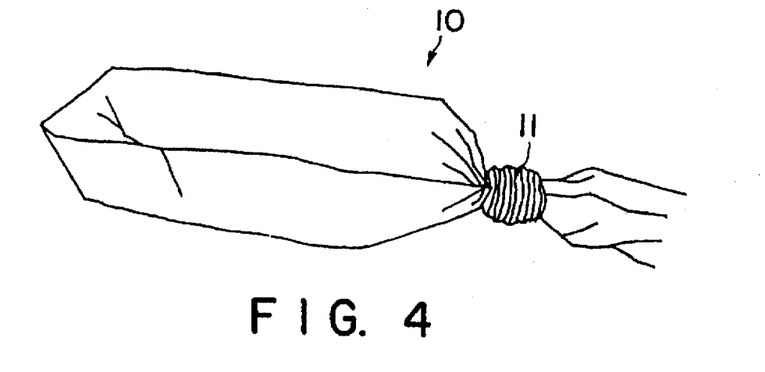
FIG. 4 illustrates a plastic film packet (¼"×1") filled with saline solution.

Referring to the drawing FIG. 4 shows a small plastic bag 10 approximately about 1" in length and ¼" in diameter which has been prefilled with water or saline and has been sealed as by a knot 11 or by heat sealing to avoid leakage of the liquid contents. The individual bags may be refrigerated until needed or they may be immersed in ice just prior to use. The tubes may also be prepared in a continuous chain (not shown), the connecting areas between bags having been sealed by heat and/or pressure. Individual bags can be separated off as then needed. The plastic used for forming the bags can be any of the conventional plastics, impermeable to liquid and suitable for insertion into the mouth.

Figure 5:
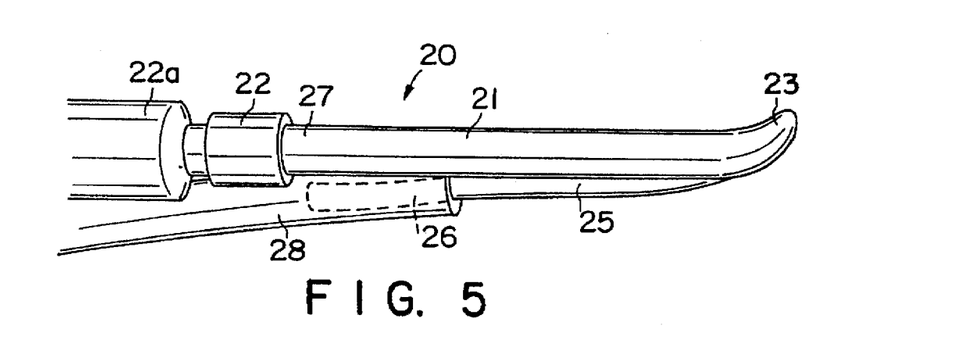
FIG. 5 illustrates a metal device consisting of two joined hollow tubes adapted for cycling of water through the two tubes.

In FIG. 5, a metal device 20 for delivering i.e., transmitting cold to the zone of intra-oral tenderness is shown. The device can be made of any non-rusting easily fabricable metal. The device is formed of a hollow metal tube 21 closed at its exposed end 23 connected to tube 25 closely adjacent to its end 23. The hollow metal tube 21 is connected to tube 25 by conventional fabrication means. Tube 21 is connected at 27 by conventional means 22 at its proximal end so that leakage of fluid does not occur when the cold water after having been perfused through the tube 25 and from there into tube 21 is returned for chilling. The cold water enters during the application of the device into indirect contact with the zone of intra-oral tenderness via the structure shown at 25, from there into tube 21 which is in contact with the intra-oral zone of tenderness, moving from that portion of the structure into the flexible tubing (not shown) for recycling to a chill zone and back to tube 25. 22a serves to facilitate gripping of the device in use.

The structure as described facilitates the continuous recycling of the water throughout the procedure. It most conveniently provides a means for removing the cold water without any attendant discomfort or inconvenience to the patient.

Figure 6:
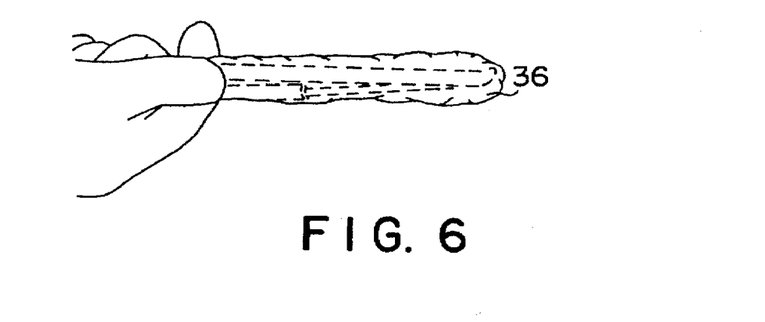
FIG. 6 illustrates a disposable plastic film sheath for use with the device of FIG. 5.
Figure 7:
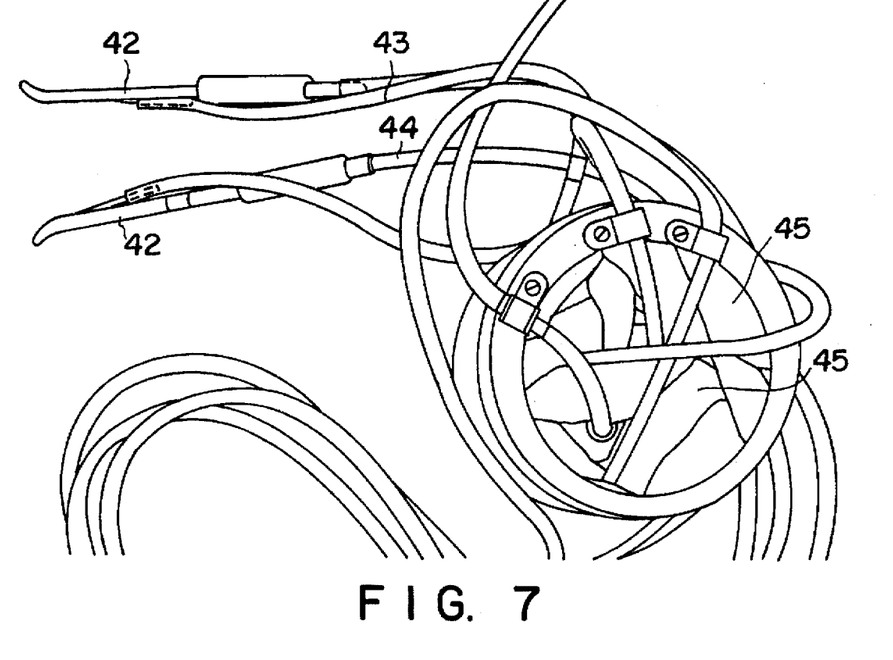
FIG. 7 illustrates two of the devices of FIG. 5 connected in such a manner as to be able to be placed bilaterally, the device being provided with suitable motorized pump means.

In FIG. 6, a disposable sheath 36 made of plastic film is shown which is dimensioned so that it will fit over the metal tubes 21 & 25, shown in FIG. 5. The plastic sheath 36 can be easily placed over the metal tube and removed therefrom. A new sheath can be applied and removed for each separate subject. In FIG. 7, two of the devices here, indicated by reference numeral 42 as also shown in FIG. 5 are provided so that the application of cold can be carried out bilaterally. The devices are provided with appropriate tubing 43 and 44 for supplying cold water or saline and for conducting the same away once used. The arrangement is best maintained within a flask or container and pumping means are provided for maintaining the circulation of the fluid. The pump is covered by ice 45 and water.

Figure 8:
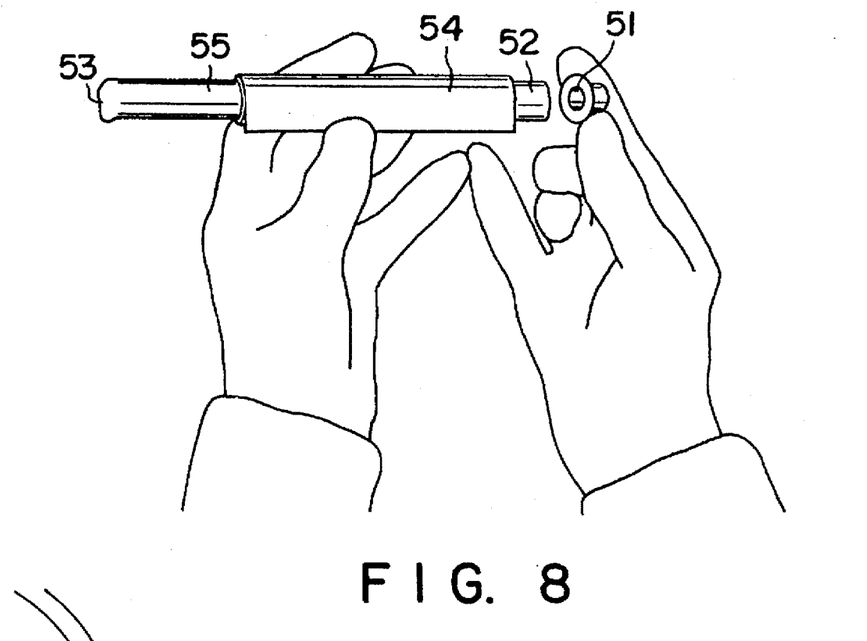
FIG. 8 illustrates a metal tube with the end shaped to adapt to the area of intra-maxillary tenderness partially enclosed within a concentrically arranged insulating tube showing the stopper adapted for insertion into the distal end of the metal tube.

FIG. 8 illustrates an embodiment of another device and as shown comprises a hollow metal tube 55 contained within an insulating sheath 54. The proximal end 53 of tube 55 which is to be applied to the zone of intra-oral tenderness is shaped for better adaptation to the area of intra-maxillary tenderness. At its opposite or distal end 52, a stop 51 for insertion into the end 52 of the device is provided which serves to retain the cold water or ice without leakage during chilling and prior to its application. Prior to use, the tube 55 is filled with water, the stopper inserted and the tube refrigerated. When the device is to be used with a patient, the end 53 is held against the area of intra-oval tenderness.

Figure 9:
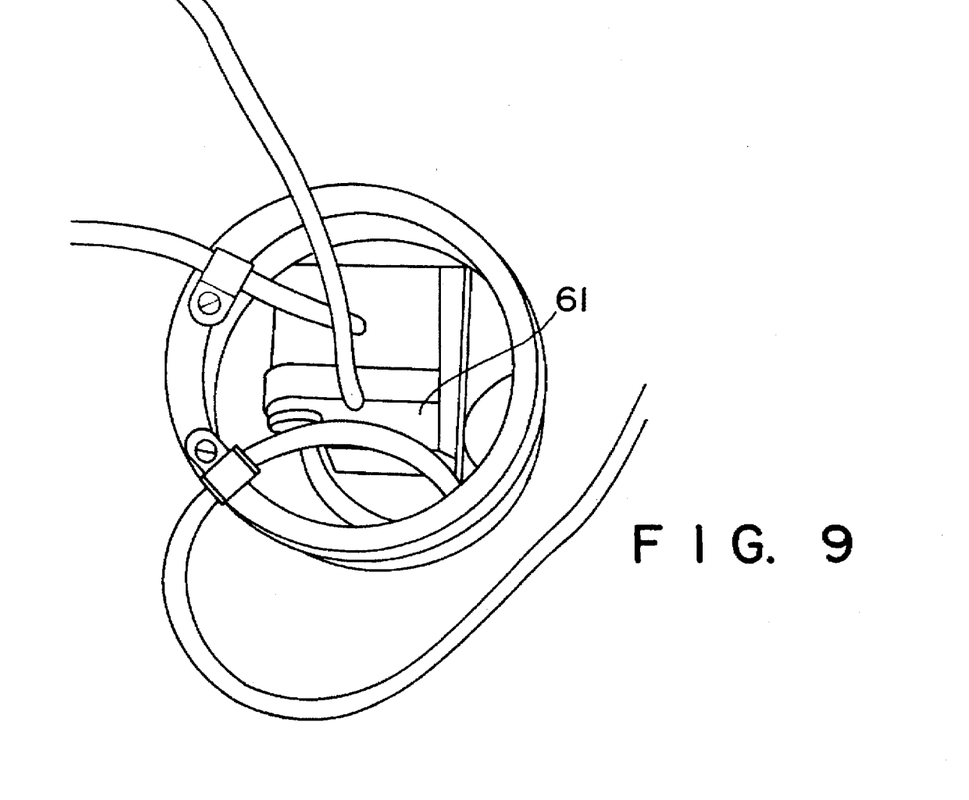
FIG. 9 illustrates another view of the device of FIG. 7 with the motorized pumping means exposed.

The pump means 61 for circulation of the cold water is shown in FIG. 9. Otherwise the device is as shown in FIG. 7.

Figure 10:
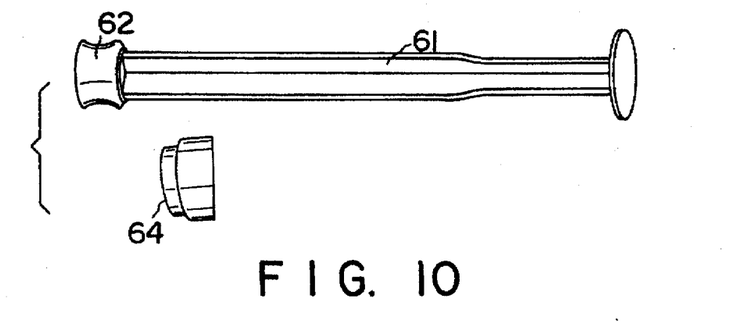
FIG. 10 illustrates two parts of an extrusion device which are, the plunger and stopper, the piston at its proximal end being provided with an attachment for facilitating extrusion, rubber stop and plastic plunger.
Figure 11:
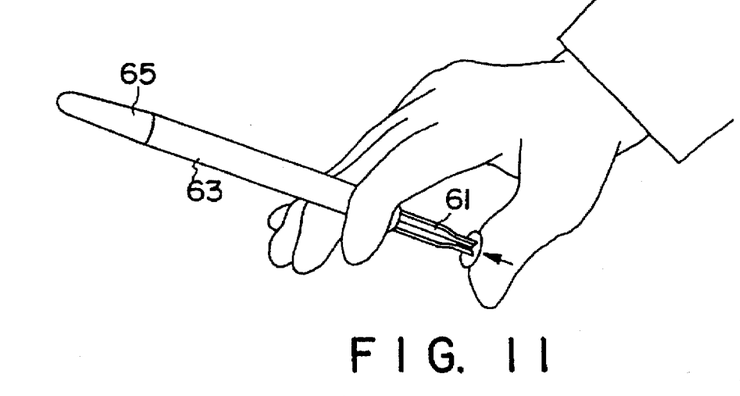
FIG. 11 shows a further embodiment of the device of FIG. 10 consisting of a hollow plastic tube assembled for use with the stopper removed, the piston inserted and the ice emerging from the device.

In FIG. 10, the stopper to be used with a hollow plastic device is shown at 64. Plunger 61 is also shown in this figure and dimensioned for being received in the hollow plastic tube 63 not shown in this drawing but shown in FIG. 11. The plunger 61 is provided with a plastic or rubber tip 62 which facilitates contact between the plunger and the ice in the hollow plastic device and permits the application of more uniform pressure of the plunger onto the ice. The hollow plastic tube will be filled with water or saline and refrigerated while maintained in an upright position for freezing the same. In use, the stopper 64 is removed, plunger 61 can then be inserted and as shown in FIG. 11 the ice 65 extruded by hand pressure on the plunger 61. The stopper 64 is applied to the hollow tube before filling with water to prevent the escape of any fluid during chilling and can also serve as a support i.e., as a stand for the device making it convenient to use particularly for making available back up applications.

Figure 12:
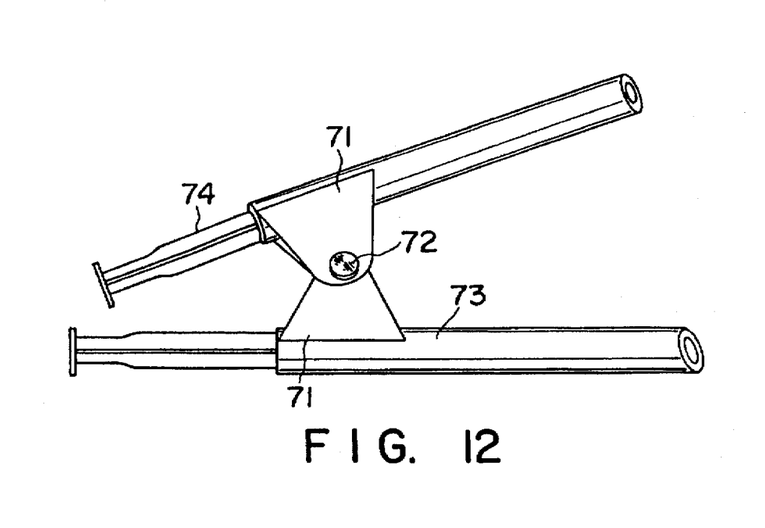
FIG. 12 shows two of the devices of FIG. 11 joined by a pivotable connecting means.

According to FIG. 12, two devices as shown in FIG. 11 are provided contained with a butterfly mounting 71 joined by an adjustable screw or pivot member 72. The mounting is adjusted through pivot 72 so that the devices can deliver cold bilaterally to the intra-oral zone of tenderness and the ice expressed by application of pressure onto the plunger 74 into and in contact with the underlying tissue. The pivot screw 72 can be set to conform to the individual anatomy of the subject being treated.

I claim:

1. A device for continuously applying cold to the zone of intra-oral tenderness located in the area of the plexus formed by the posterior and middle superior alveolar branches of the ipsilateral maxillary nerve of a subject comprising a first hollow metal tube closed at its proximal end, said proximal end being shaped for contact with the zone of intra-oral tenderness, a second hollow metal tube external to said first hollow metal tube and joined to said first hollow metal tube closely adjacent to the proximal end of said first metal tube, said second metal tube being adapted for supplying cold liquid into said first metal tube for passage therethrough, first flexible tubing means connected to the distal end of said first metal tube for recycling liquid after its passage through said first metal tube into a chilling zone, second flexible tubing means connected to said second metal tube for introducing cold liquid into said second metal tube and pumping means being provided for circulating said liquid through said second flexible tubing means into first said second metal tube, then into said first metal tube, then into said first flexible tube, then into said first flexible tubing means wherein two of said devices are connected by a means effective to mount said devices in a position effective to provide the application of cold bilaterally to a patient in need of the application of said cold.

\* \* \* \* \*